(12) United States Patent
Schwarz et al.

(10) Patent No.: US 9,867,829 B2
(45) Date of Patent: Jan. 16, 2018

(54) STABLE PHARMACEUTICAL COMPOSITION CONTAINING 8-[(3R)-3-AMINO-1-PIPERIDINYL]-7-(2-BUTYN-1-YL)-3,7-DIHYDRO-3-METHYL-1-[(4-METHYL-2-QUINAZOLINYL)METHYL]-1H-PURINE-2,6-DIONE OR A PHARMACEUTICALLY ACCEPTABLE SALT THEREOF

(71) Applicant: Sandoz AG, Basel (CH)

(72) Inventors: Franz X. Schwarz, Kundl (AT); Georg Anker, Kundl (AT); Johann Bacher, Kundl (AT); Andreas Hotter, Kundl (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/417,992

(22) PCT Filed: Aug. 12, 2013

(86) PCT No.: PCT/EP2013/066777
§ 371 (c)(1),
(2) Date: Jan. 28, 2015

(87) PCT Pub. No.: WO2014/026939
PCT Pub. Date: Feb. 20, 2014

(65) Prior Publication Data
US 2015/0224102 A1    Aug. 13, 2015

(30) Foreign Application Priority Data

Aug. 13, 2012 (EP) .................................. 12180257

(51) Int. Cl.
| | | |
|---|---|---|
| A61K 31/522 | (2006.01) | |
| A61K 9/28 | (2006.01) | |
| B65D 75/36 | (2006.01) | |
| A61J 1/00 | (2006.01) | |
| B65D 65/38 | (2006.01) | |
| A61K 31/155 | (2006.01) | |
| A61K 9/20 | (2006.01) | |

(52) U.S. Cl.
CPC .............. *A61K 31/522* (2013.01); *A61J 1/00* (2013.01); *A61K 9/2013* (2013.01); *A61K 9/2018* (2013.01); *A61K 9/2027* (2013.01); *A61K 9/2059* (2013.01); *A61K 9/2095* (2013.01); *A61K 9/2866* (2013.01); *A61K 31/155* (2013.01); *B65D 65/38* (2013.01); *B65D 75/36* (2013.01); *B65D 2565/388* (2013.01)

(58) Field of Classification Search
None
See application file for complete search history.

(56) References Cited

U.S. PATENT DOCUMENTS

| | | | | |
|---|---|---|---|---|
| 2010/0209506 A1 | 8/2010 | Eisenreich | | |
| 2012/0094894 A1* | 4/2012 | Graefe-Mody | ....... | A61K 9/0019 514/1.9 |
| 2012/0107398 A1* | 5/2012 | Schneider | .............. | A61K 9/209 424/465 |
| 2013/0107398 A1* | 5/2013 | Weber | .................. | B60N 2/4415 361/2 |
| 2015/0051228 A1* | 2/2015 | Dwivedi | .............. | C07D 473/06 514/263.21 |

FOREIGN PATENT DOCUMENTS

| | | |
|---|---|---|
| JP | 2009535375 | 10/2009 |
| JP | 2012512848 | 6/2012 |
| JP | 2012517458 | 8/2012 |
| WO | WO 2004/018468 | * 3/2004 |
| WO | 2004/018468 | 4/2004 |
| WO | 2004/127724 | 11/2007 |
| WO | 2007/128721 | 11/2007 |
| WO | WO 2007/28721 | * 11/2007 |
| WO | 2009/121945 | 10/2009 |
| WO | 2010/072776 | 7/2010 |
| WO | 2011/039367 | 4/2011 |
| WO | 2011/138380 | 11/2011 |

OTHER PUBLICATIONS

International Search Report issued in PCT/EP2013/06677, dated Dec. 9, 2013, pp. 1-2.
Written Opinion issued in PCT/EP2013/06677, dated Dec. 9, 2013, pp. 1-11.
Office Action issued in corresponding Japanese Patent Application No. 2015-526952, dated May 9, 2017, and translation thereof pp. 1-7.

* cited by examiner

*Primary Examiner* — Robert A Wax
*Assistant Examiner* — Danah Al-Awadi
(74) *Attorney, Agent, or Firm* — Jeffrey S. Melcher; Manelli Selter PLLC (57) ABSTRACT

The present invention relates to a stable pharmaceutical composition comprising amorphous or crystalline linagliptin or a pharmaceutically acceptable salt of linagliptin, mannitol, copovidone, and magnesium stearate, processes for preparing the stable pharmaceutical composition, and a container comprising the stable pharmaceutical composition.

21 Claims, 3 Drawing Sheets

STABLE PHARMACEUTICAL COMPOSITION CONTAINING 8-[(3R)-3-AMINO-1-PIPERIDINYL]-7-(2-BUTYN-1-YL)-3,7-DIHYDRO-3-METHYL-1-[(4-METHYL-2-QUINAZOLINYL)METHYL]-1H-PURINE-2,6-DIONE OR A PHARMACEUTICALLY ACCEPTABLE SALT THEREOF

FIELD OF THE INVENTION

The present invention relates to a stable pharmaceutical composition comprising 8-[(3R)-3-amino-1-piperidinyl]-7-(2-butyn-1-yl)-3,7-dihydro-3-methyl-1-[(4-methyl-2-quinazolinyl)methyl]-1H-purine-2,6-dione (linagliptin) or a pharmaceutically acceptable salt thereof, mannitol, copovidone, and magnesium stearate; processes for preparing the stable pharmaceutical composition; and a container comprising the stable pharmaceutical composition.

BACKGROUND OF THE INVENTION

Linagliptin (8-[(3R)-3-Amino-1-piperidinyl]-7-(2-butyn-1-yl)-3,7-dihydro-3-methyl-1-[(4-methyl-2-quinazolinyl)methyl]-1H-purine-2,6-dione) acts as a dipeptidyl peptidase IV (DPP IV) inhibitor and is used for the once-daily oral treatment of type 2 diabetes.

WO2004/018468 discloses linagliptin, salts thereof, processes for the preparation of linagliptin and its salts, and the use of linagliptin and its salts for the treatment of diseases, such as, for example, type 1 diabetes, type 2 diabetes, adipositas, arthritis, and calcitonin-caused osteoporosis.

WO2007/128721 describes crystalline forms A, B, C, D and E of linagliptin and processes for preparing the crystalline forms. WO2007/128721 also discloses that linagliptin prepared according to WO2004/018468 is obtained in the form of a mixture of crystalline form A and crystalline form B.

WO2007/128724 discloses a pharmaceutical composition comprising a DPP IV inhibitor compound with an amino group or a salt thereof, a first diluent, a second diluent, a binder, a disintegrant and a lubricant. According to WO2007/128724 it has been observed, that DPP IV inhibitors with a primary or secondary amino group show incompatibilities, degradation problems, or extraction problems with a number of customary excipients such as microcrystalline cellulose, sodium starch glycolate, croscarmellose sodium, tartaric acid, citric acid, glucose, fructose, saccharose, lactose, and maltodextrines. Though the compounds themselves are very stable, they are considered to react with many excipients used in solid dosage forms and with impurities of excipients, especially in tight contact provided in tablets and at high excipient/drug ratios. It is assumed that the amino group reacts with reducing sugars and with other reactive carbonyl groups and with carboxylic acid functional groups formed for example at the surface of microcrystalline cellulose by oxidation. These problems have been primarily observed in low dosage ranges and have been solved according to WO2007/128724 by the described pharmaceutical composition comprising a DPP IV inhibitor compound with an amino group or a salt thereof, a first diluent, a second diluent, a binder, a disintegrant and a lubricant.

SUMMARY OF THE INVENTION

It has now been found that the pharmaceutical compositions described in WO2007/128724 are characterized by low stability in a humid environment. In particular, the compositions according to WO2007/128724 show a reduced dissolution after storage under humid conditions. This reduced dissolution significantly lowers the bioavailability of the active ingredient. Accordingly, the conditions under which these compositions need to be stored and handled have to be controlled carefully. Moreover, the compositions need to be packed in moisture tight containers. These requirements represent a problem in particular in countries where the climate is humid. Moreover, these requirements make the production, handling, storage and packaging of the formulations expensive and economically unattractive in a number of countries.

DETAILED DESCRIPTION OF THE INVENTION

The present invention provides a pharmaceutical composition which is stable and shows a favorable dissolution profile after storage under humid conditions. The pharmaceutical composition of the present invention can thus be manufactured without controlling the humidity in the production facilities, it can be handled without special precautions, it can be packed in inexpensive packaging materials and it can be used without limitations in a wide range of countries independently of the climate conditions.

In particular, the pharmaceutical composition of the present invention can be manufactured, handled and stored in a country having areas with an Af or Am climate according to the Koppen-Geiger climate classification without any detriment to the pharmaceutical effectiveness of the pharmaceutical composition.

The pharmaceutical composition of the present invention comprises linagliptin or a pharmaceutically acceptable salt thereof, mannitol, copovidone, and magnesium stearate.

Preferably, the pharmaceutical composition of the present invention comprises linagliptin or a pharmaceutically acceptable salt thereof, mannitol, copovidone, crospovidone, and magnesium stearate.

Copovidone is a copolymer of vinylpyrrolidone with other vinyl derivates. A preferred copovidone is the copolymer of vinylpyrrolidone and vinyl acetate. A particularly preferred copovidone is the copolymer of vinylpyrrolidone and vinylacetate in a ratio of 60/40% by weight. Examples include Kollidon VA 64, KoVidone VA64, Luviskol VA 64, and Plasdone S 630. A preferred example is Kollidon VA 64.

Crospovidone is a cross-linked polyvinylpyrrolidone. It is formed by so-called popcorn-polymerization of vinylpyrrolidone. Examples of crospovidone include Kollidon CL, Kollidon CL-M, PolyKoVidone, Polyplasdone XL and Polyplasdone XL-10. A preferred example is Polyplasdone XL.

The pharmaceutical composition of the present invention can further comprise additional diluents such as cellulose powder, anhydrous dibasic calcium phosphate, dibasic calcium phosphate dihydrate, erythritol, hydroxypropyl cellulose, xylitol and/or pregelatinized starch.

The pharmaceutical composition of the present invention can further comprise additional binders such as hydroxypropyl methylcellulose, hydroxypropylcellulose, substituted hydroxypropylcellulose and/or polyvinylpyrrolidone.

The pharmaceutical composition of the present invention can further comprise additional lubricants, such as talc, polyethylene glycol, calcium behenate, calcium stearate and/or hydrogenated castor oil.

The pharmaceutical composition of the present invention can further comprise a glidant, for example, colloidal silicon dioxide.

The pharmaceutical composition of the present invention can further comprise a colorant, for example, ferric oxide.

Preferably, the pharmaceutical composition of the present invention comprises a core consisting of linagliptin or a pharmaceutically acceptable salt thereof, mannitol, copovidone and magnesium stearate.

More preferably, the pharmaceutical composition of the present invention comprises a core and a coating, the core consisting of linagliptin or a pharmaceutically acceptable salt thereof, mannitol, copovidone and magnesium stearate.

In a further preferred embodiment, the pharmaceutical composition of the present invention comprises a core and a coating, wherein the core consists of linagliptin or a pharmaceutically acceptable salt thereof, mannitol, copovidone and magnesium stearate, and wherein the coating comprises hydroxypropyl methylcellulose, polyethylenglycol, talc, and titanium dioxide.

In a further preferred embodiment, the pharmaceutical composition of the present invention comprises a core and a coating, wherein the core consists of linagliptin or a pharmaceutically acceptable salt thereof, mannitol, copovidone and magnesium stearate, and wherein the coating comprises hydroxypropyl methylcellulose, polyethylenglycol, talc, titanium dioxide, and a colorant.

In a further preferred embodiment, the pharmaceutical composition of the present invention comprises a core and a coating, wherein the core consists of linagliptin or a pharmaceutically acceptable salt thereof, mannitol, copovidone and magnesium stearate, and wherein the coating comprises hydroxypropyl methylcellulose, polyethylenglycol, talc, titanium dioxide, and ferric oxide.

In another preferred embodiment, the pharmaceutical composition of the present invention comprises a core consisting of linagliptin or a pharmaceutically acceptable salt thereof, mannitol, copovidone, crospovidone and magnesium stearate.

More preferably, the pharmaceutical composition of the present invention comprises a core and a coating, the core consisting of linagliptin or a pharmaceutically acceptable salt thereof, mannitol, copovidone, crospovidone and magnesium stearate.

In a further preferred embodiment, the pharmaceutical composition of the present invention comprises a core and a coating, wherein the core consists of linagliptin or a pharmaceutically acceptable salt thereof, mannitol, copovidone, crospovidone and magnesium stearate, and wherein the coating comprises hydroxypropyl methylcellulose, polyethylenglycol, talc, and titanium dioxide.

In a further preferred embodiment, the pharmaceutical composition of the present invention comprises a core and a coating, wherein the core consists of linagliptin or a pharmaceutically acceptable salt thereof, mannitol, copovidone, crospovidone and magnesium stearate, and wherein the coating comprises hydroxypropyl methylcellulose, polyethylenglycol, talc, titanium dioxide, and a colorant.

In a further preferred embodiment, the pharmaceutical composition of the present invention comprises a core and a coating, wherein the core consists of linagliptin or a pharmaceutically acceptable salt thereof, mannitol, copovidone, crospovidone and magnesium stearate, and wherein the coating comprises hydroxypropyl methylcellulose, polyethylenglycol, talc, titanium dioxide, and ferric oxide.

In a further preferred embodiment, the pharmaceutical composition of the present invention comprises linagliptin in amorphous form.

In a further preferred embodiment, the pharmaceutical composition of the present invention comprises crystalline linagliptin having polymorphic form A.

In a further preferred embodiment, the pharmaceutical composition of the present invention comprises crystalline linagliptin having polymorphic form B.

In a further preferred embodiment, the pharmaceutical composition of the present invention comprises crystalline linagliptin having polymorphic form C.

In a further preferred embodiment, the pharmaceutical composition of the present invention comprises a mixture of crystalline linagliptin having polymorphic form A and crystalline linagliptin having polymorphic form B.

In a further preferred embodiment, the pharmaceutical composition of the present invention comprises linagliptin in amorphous form, mannitol, copovidone, and magnesium stearate.

In a further preferred embodiment, the pharmaceutical composition of the present invention comprises linagliptin in amorphous form, mannitol, copovidone, crospovidone, and magnesium stearate.

In a further preferred embodiment, the pharmaceutical composition of the present invention comprises a core and a coating, the core consisting of linagliptin in amorphous form, mannitol, copovidone and magnesium stearate.

In a further preferred embodiment, the pharmaceutical composition of the present invention comprises a core and a coating, the core consisting of linagliptin in amorphous form, mannitol, copovidone, crospovidone and magnesium stearate.

In a further preferred embodiment, the pharmaceutical composition of the present invention comprises crystalline linagliptin having polymorphic form A, mannitol, copovidone, and magnesium stearate.

In a further preferred embodiment, the pharmaceutical composition of the present invention comprises crystalline linagliptin having polymorphic form A, mannitol, copovidone, crospovidone, and magnesium stearate.

In a further preferred embodiment, the pharmaceutical composition of the present invention comprises a core and a coating, the core consisting of crystalline linagliptin having polymorphic form A, mannitol, copovidone and magnesium stearate.

In a further preferred embodiment, the pharmaceutical composition of the present invention comprises a core and a coating, the core consisting of crystalline linagliptin having polymorphic form A, mannitol, copovidone, crospovidone and magnesium stearate.

In a further preferred embodiment, the pharmaceutical composition of the present invention comprises a mixture of crystalline linagliptin having polymorphic form A and crystalline Iinagliptin having polymorphic form B, mannitol, copovidone, and magnesium stearate.

In a further preferred embodiment, the pharmaceutical composition of the present invention comprises a mixture of crystalline linagliptin having polymorphic form A and crystalline linagliptin having polymorphic form B, mannitol, copovidone, crospovidone, and magnesium stearate.

In a further preferred embodiment, the pharmaceutical composition of the present invention comprises a core and a coating, the core consisting of a mixture of crystalline Iinagliptin having polymorphic form A and crystalline linagliptin having polymorphic form B, mannitol, copovidone and magnesium stearate.

In a further preferred embodiment, the pharmaceutical composition of the present invention comprises a core and a coating, the core consisting of a mixture of crystalline linagliptin having polymorphic form A and crystalline linagliptin having polymorphic form B, mannitol, copovidone, crospovidone and magnesium stearate.

Linagliptin can be prepared according to the process described in WO2004/018468. Pharmaceutically acceptable salts of linagliptin can be prepared according to WO2004/018468 or WO2010/072776. A particularly preferred pharmaceutically acceptable salt of linagliptin is the benzoate salt having polymorphic form II which can be prepared as follows: (a) dissolving linagliptin benzoate (as prepared according to WO2010/072776) in acetonitrile at a concentration ranging from about 10 g/l to 20 g/l upon heating, for example from 50° C. to 82° C.; (b) optionally filtering the solution; (c) cooling the solution at a cooling rate of ≤−1° C./min in order to induce crystallization at a temperature starting above 35° C.; (d) isolating the obtained crystals; and (e) optionally drying the crystals.

Linagliptin polymorphic forms A, B and C are defined in WO2007/128721 and can be prepared by the processes described in WO2007/128721 from linagliptin obtained according to the process described in WO2004/018468 as starting material.

Linagliptin prepared by the process as described in WO2004/018468 is obtained in the form of a mixture of polymorphs A and B.

A mixture of crystalline linagliptin polymorphic form A and crystalline linagliptin polymorphic form B can also be obtained by mixing crystalline linagliptin polymorphic form A prepared according to WO2007/128721 with crystalline linagliptin polymorphic form B prepared according to WO2007/128721.

Amorphous linagliptin can be prepared by a process comprising the steps of
a) dissolving linagliptin in a suitable solvent, and
b) evaporating the solution obtained in step a) to dryness.

Any crystalline form of linagliptin may be applied as starting material in step a) of the above described process, e.g. crystalline linagliptin having polymorphic form A, B, C, D or E of WO 2007/128721 or mixtures thereof. Most preferably a mixture of crystalline linagliptin having polymorphic form A and crystalline linagliptin having polymorphic form B as obtained by the process disclosed in WO2004/018468 can be used.

Suitable solvents which may be applied in step a) of the above described process are e.g. methanol, ethanol, n-propanol, isopropanol, methyl acetate, ethyl acetate, acetone, isobutylmethyl ketone, dichloromethane, chloroform, tetrahydrofuran and/or acetonitrile, with dichloromethane being preferred.

In step a) of the above described process a mixture of linagliptin and a suitable solvent is preferably prepared at a concentration which ensures that the whole linagliptin starting material is completely dissolved. The dissolution step a) may be performed at a temperature ranging from about 25 to 80° C., more preferably from about 25 to 60° C. and most preferably from about 25 to 50° C. Optionally an additional filtration step or a charcoal treatment or a charcoal treatment followed by a filtration step may be applied.

Thereafter, in step b), the obtained solution is evaporated to dryness preferably under reduced pressure of ≤900 mbar (such as >500 mbar and ≤900 mbar), more preferably ≤800 mbar (such as >500 mbar and ≤800 mbar) and most preferably ≤600 mbar (such as >500 mbar and ≤600 mbar). The temperature during evaporation may range from about 25 to 80° C., more preferably from about 25 to 60° C. and most preferably from about 25 to 50° C.

The obtained solid material may be further dried preferably under reduced pressure such as ≤500 mbar (such as ≥10 mbar and ≤500 mbar), more preferably ≤100 mbar (such as ≥10 mbar and ≤100 mbar) and most preferably ≤50 mbar (such as ≥10 mbar and ≤50 mbar) at a temperature preferably ranging from about 20 to 80° C., more preferably from about 20 to 60° C. and most preferably from about 20 to 40° C., preferably over 6 to 48 hours, more preferably over 12 to 36 hours, most preferably over 18 to 24 hours.

A particularly preferred process for preparing amorphous linagliptin comprises:
a) dissolving linagliptin in dichloromethane at a temperature in the range of from 25 to 80° C.,
b) evaporating the solution obtained in step a) to dryness at a temperature in the range of from 25 to 80° C. under a reduced pressure of ≤900 mbar (preferably >500 mbar and ≤900 mbar), and
c) optionally, drying the product obtained in step b) at a temperature in the range of from 25 to 80° C. under a reduced pressure of ≤500 mbar (preferably ≥10 mbar and ≤500 mbar) for 6 to 48 hours.

The XRPD of amorphous linagliptin shows an amorphous halo. A representative diffractogram is displayed in FIG. 2.

Figure 3:
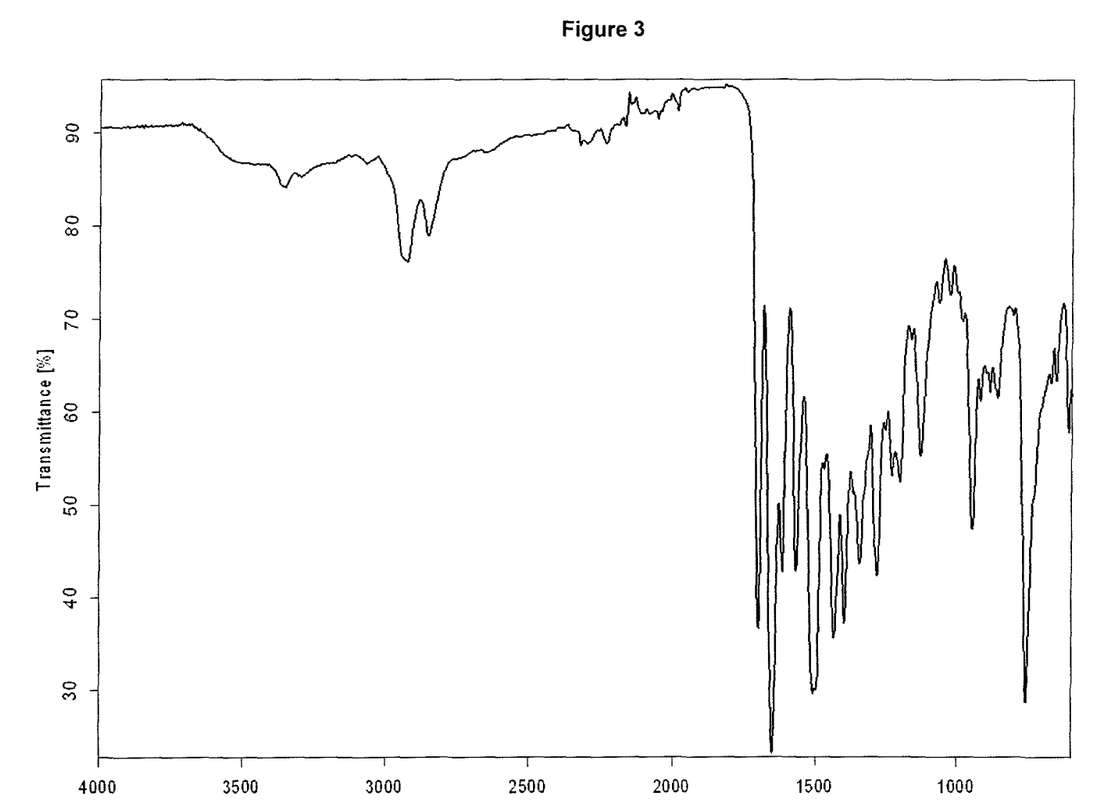
FIG. 3: Fourier transform infrared (FTIR) spectrum of amorphous linagliptin prepared according to Example 8

Amorphous linagliptin may optionally be further characterized by an FTIR spectrum comprising characteristic peaks at $2923\pm2$ cm$^{-1}$, $1650\pm2$ cm$^{-1}$, $1568\pm2$ cm$^{-1}$, $1344\pm2$ cm$^{-1}$ and $759\pm2$ cm$^{-1}$. More preferably, the amorphous linagliptin is characterized by an FTIR spectrum comprising characteristic peaks at $2923\pm2$ cm$^{-1}$, $2851\pm2$ cm$^{-1}$, $1698\pm2$ cm$^{-1}$, $1650\pm2$ cm$^{-1}$, $1615\pm2$ cm$^{-1}$, $1568\pm2$ cm$^{-1}$, $1508\pm2$ cm$^{-1}$, $1434\pm2$ cm$^{-1}$, $1398\pm2$ cm$^{-1}$, $1344\pm2$ cm$^{-1}$, $1282\pm2$ cm$^{-1}$, $1128\pm2$ cm$^{-1}$, $947\pm2$ cm$^{-1}$, $759\pm2$ cm$^{-1}$ and $613\pm2$ cm$^{-1}$. A representative FTIR spectrum is displayed in FIG. 3.

Linagliptin or the pharmaceutically acceptable salt thereof can be present in the pharmaceutical composition according to the present invention in an amount of from 0.1 to 100 mg (based on the free base in case of a pharmaceutically acceptable salt). Preferably, the pharmaceutical composition according to the present invention contains 0.5 mg, 1 mg, 2.5 mg, 5 mg or 10 mg of linagliptin or the pharmaceutically acceptable salt thereof (based on the free base in case of a pharmaceutically acceptable salt).

Mannitol is preferably present in the pharmaceutical composition according to the present invention in an amount of from 75.0 to 95% by weight, based on the pharmaceutical composition, more preferably 80 to 95% by weight, based on the pharmaceutical composition, most preferably 90 to 95% by weight, based on the pharmaceutical composition. Copovidone is preferably present in the pharmaceutical composition according to the present invention in an amount of from 1 to 10% by weight, based on the pharmaceutical composition, more preferably in an amount of from 1 to 5% by weight, based on the pharmaceutical composition. Crospovidone is preferably present in the pharmaceutical composition according to the present invention in an amount of from 1 to 15% by weight, more preferably in an amount of from 1 to 5% by weight, based on the pharmaceutical composition. Magnesium stearate is preferably present in the pharmaceutical composition according to the present invention in an amount of from 0.3 to 5% by weight, based on the pharmaceutical composition, more preferably in an amount of from 0.3 to 3% by weight, based on the pharmaceutical composition.

In a preferred embodiment, the pharmaceutical composition according to the present invention comprises linagliptin or a pharmaceutically acceptable salt thereof, mannitol, copovidone, and magnesium stearate, wherein the mannitol is present in an amount of 75.0 to 95% by weight, based on the pharmaceutical composition.

In a further preferred embodiment, the pharmaceutical composition according to the present invention comprises linagliptin or a pharmaceutically acceptable salt thereof, mannitol, copovidone, and magnesium stearate, wherein the mannitol is present in an amount of 80 to 95% by weight, based on the pharmaceutical composition.

In a further preferred embodiment, the pharmaceutical composition according to the present invention comprises linagliptin or a pharmaceutically acceptable salt thereof, mannitol, copovidone, and magnesium stearate, wherein the mannitol is present in an amount of 90 to 95% by weight, based on the pharmaceutical composition.

In a further preferred embodiment, the pharmaceutical composition according to the present invention comprises linagliptin or a pharmaceutically acceptable salt thereof, mannitol, copovidone, crospovidone and magnesium stearate, wherein the mannitol is present in an amount of 75.0 to 95% by weight, based on the pharmaceutical composition.

In a further preferred embodiment, the pharmaceutical composition according to the present invention comprises linagliptin or a pharmaceutically acceptable salt thereof, mannitol, copovidone, crospovidone and magnesium stearate, wherein the mannitol is present in an amount of 80 to 95% by weight, based on the pharmaceutical composition.

In a further preferred embodiment, the pharmaceutical composition according to the present invention comprises linagliptin or a pharmaceutically acceptable salt thereof, mannitol, copovidone, crospovidone and magnesium stearate, wherein the mannitol is present in an amount of 90 to 95% by weight, based on the pharmaceutical composition.

In a further preferred embodiment, the pharmaceutical composition according to the present invention comprises linagliptin in amorphous form, mannitol, copovidone, and magnesium stearate, wherein the mannitol is present in an amount of 75.0 to 95% by weight, based on the pharmaceutical composition.

In a further preferred embodiment, the pharmaceutical composition according to the present invention comprises linagliptin in amorphous form, mannitol, copovidone, and magnesium stearate, wherein the mannitol is present in an amount of 80 to 95% by weight, based on the pharmaceutical composition.

In a further preferred embodiment, the pharmaceutical composition according to the present invention comprises linagliptin in amorphous form, mannitol, copovidone, and magnesium stearate, wherein the mannitol is present in an amount of 90 to 95% by weight, based on the pharmaceutical composition.

In a further preferred embodiment, the pharmaceutical composition according to the present invention comprises linagliptin in amorphous form, mannitol, copovidone, crospovidone and magnesium stearate, wherein the mannitol is present in an amount of 75.0 to 95% by weight, based on the pharmaceutical composition.

In a further preferred embodiment, the pharmaceutical composition according to the present invention comprises linagliptin in amorphous form, mannitol, copovidone, crospovidone and magnesium stearate, wherein the mannitol is present in an amount of 80 to 95% by weight, based on the pharmaceutical composition.

In a further preferred embodiment, the pharmaceutical composition according to the present invention comprises linagliptin in amorphous form, mannitol, copovidone, crospovidone and magnesium stearate, wherein the mannitol is present in an amount of 90 to 95% by weight, based on the pharmaceutical composition.

In a further preferred embodiment, the pharmaceutical composition according to the present invention comprises linagliptin, mannitol, copovidone, and magnesium stearate,
wherein the linagliptin is present as a mixture of crystalline linagliptin having polymorphic form A and crystalline linagliptin having polymorphic form B, and
wherein the mannitol is present in an amount of 75.0 to 95% by weight, based on the pharmaceutical composition.

In a further preferred embodiment, the pharmaceutical composition according to the present invention comprises linagliptin, mannitol, copovidone, and magnesium stearate,
wherein the linagliptin is present as a mixture of crystalline linagliptin having polymorphic form A and crystalline linagliptin having polymorphic form B, and
wherein the mannitol is present in an amount of 80 to 95% by weight, based on the pharmaceutical composition.

In a further preferred embodiment, the pharmaceutical composition according to the present invention comprises linagliptin, mannitol, copovidone, and magnesium stearate,
wherein the linagliptin is present as a mixture of crystalline linagliptin having polymorphic form A and crystalline linagliptin having polymorphic form B, and
wherein the mannitol is present in an amount of 90 to 95% by weight, based on the pharmaceutical composition.

In a further preferred embodiment, the pharmaceutical composition according to the present invention comprises linagliptin, mannitol, copovidone, crospovidone and magnesium stearate,
wherein the linagliptin is present as a mixture of crystalline linagliptin having polymorphic form A and crystalline linagliptin having polymorphic form B, and
wherein the mannitol is present in an amount of 75.0 to 95% by weight, based on the pharmaceutical composition.

In a further preferred embodiment, the pharmaceutical composition according to the present invention comprises linagliptin, mannitol, copovidone, crospovidone and magnesium stearate,
wherein the linagliptin is present as a mixture of crystalline linagliptin having polymorphic form A and crystalline linagliptin having polymorphic form B, and
wherein the mannitol is present in an amount of 80 to 95% by weight, based on the pharmaceutical composition.

In a further preferred embodiment, the pharmaceutical composition according to the present invention comprises linagliptin, mannitol, copovidone, crospovidone and magnesium stearate,
wherein the linagliptin is present as a mixture of crystalline linagliptin having polymorphic form A and crystalline linagliptin having polymorphic form B, and
wherein the mannitol is present in an amount of 90 to 95% by weight, based on the pharmaceutical composition.

In a further preferred embodiment, the pharmaceutical composition according to the present invention comprises crystalline linagliptin having polymorphic form A, mannitol, copovidone, and magnesium stearate, wherein the mannitol is present in an amount of 75.0 to 95% by weight, based on the pharmaceutical composition.

In a further preferred embodiment, the pharmaceutical composition according to the present invention comprises crystalline linagliptin having polymorphic form A, mannitol, copovidone, and magnesium stearate, wherein the mannitol is present in an amount of 80 to 95% by weight, based on the pharmaceutical composition.

In a further preferred embodiment, the pharmaceutical composition according to the present invention comprises crystalline linagliptin having polymorphic form A, mannitol, copovidone, and magnesium stearate, wherein the mannitol is present in an amount of 90 to 95% by weight, based on the pharmaceutical composition.

In a further preferred embodiment, the pharmaceutical composition according to the present invention comprises crystalline linagliptin having polymorphic form A, mannitol, copovidone, crospovidone and magnesium stearate, wherein the mannitol is present in an amount of 75.0 to 95% by weight, based on the pharmaceutical composition.

In a further preferred embodiment, the pharmaceutical composition according to the present invention comprises crystalline linagliptin having polymorphic form A, mannitol, copovidone, crospovidone and magnesium stearate, wherein the mannitol is present in an amount of 80 to 95% by weight, based on the pharmaceutical composition.

In a further preferred embodiment, the pharmaceutical composition according to the present invention comprises crystalline linagliptin having polymorphic form A, mannitol, copovidone, crospovidone and magnesium stearate, wherein the mannitol is present in an amount of 90 to 95% by weight, based on the pharmaceutical composition.

In a further preferred embodiment, the pharmaceutical composition according to the present invention comprises crystalline linagliptin having polymorphic form B, mannitol, copovidone, and magnesium stearate, wherein the mannitol is present in an amount of 75.0 to 95% by weight, based on the pharmaceutical composition.

In a further preferred embodiment, the pharmaceutical composition according to the present invention comprises crystalline linagliptin having polymorphic form B, mannitol, copovidone, and magnesium stearate, wherein the mannitol is present in an amount of 80 to 95% by weight, based on the pharmaceutical composition.

In a further preferred embodiment, the pharmaceutical composition according to the present invention comprises crystalline linagliptin having polymorphic form B, mannitol, copovidone, and magnesium stearate, wherein the mannitol is present in an amount of 90 to 95% by weight, based on the pharmaceutical composition.

In a further preferred embodiment, the pharmaceutical composition according to the present invention comprises crystalline linagliptin having polymorphic form B, mannitol, copovidone, crospovidone and magnesium stearate, wherein the mannitol is present in an amount of 75.0 to 95% by weight, based on the pharmaceutical composition.

In a further preferred embodiment, the pharmaceutical composition according to the present invention comprises crystalline linagliptin having polymorphic form B, mannitol, copovidone, crospovidone and magnesium stearate, wherein the mannitol is present in an amount of 80 to 95% by weight, based on the pharmaceutical composition.

In a further preferred embodiment, the pharmaceutical composition according to the present invention comprises crystalline linagliptin having polymorphic form B, mannitol, copovidone, crospovidone and magnesium stearate, wherein the mannitol is present in an amount of 90 to 95% by weight, based on the pharmaceutical composition.

In a further preferred embodiment, the pharmaceutical composition according to the present invention comprises crystalline linagliptin having polymorphic form C, mannitol, copovidone, and magnesium stearate, wherein the mannitol is present in an amount of 75.0 to 95% by weight, based on the pharmaceutical composition.

In a further preferred embodiment, the pharmaceutical composition according to the present invention comprises crystalline linagliptin having polymorphic form C, mannitol, copovidone, and magnesium stearate, wherein the mannitol is present in an amount of 80 to 95% by weight, based on the pharmaceutical composition.

In a further preferred embodiment, the pharmaceutical composition according to the present invention comprises crystalline linagliptin having polymorphic form C, mannitol, copovidone, and magnesium stearate, wherein the mannitol is present in an amount of 90 to 95% by weight, based on the pharmaceutical composition.

In a further preferred embodiment, the pharmaceutical composition according to the present invention comprises crystalline linagliptin having polymorphic form C, mannitol, copovidone, crospovidone and magnesium stearate, wherein the mannitol is present in an amount of 75.0 to 95% by weight, based on the pharmaceutical composition.

In a further preferred embodiment, the pharmaceutical composition according to the present invention comprises crystalline linagliptin having polymorphic form C, mannitol, copovidone, crospovidone and magnesium stearate, wherein the mannitol is present in an amount of 80 to 95% by weight, based on the pharmaceutical composition.

In a further preferred embodiment, the pharmaceutical composition according to the present invention comprises crystalline linagliptin having polymorphic form C, mannitol, copovidone, crospovidone and magnesium stearate, wherein the mannitol is present in an amount of 90 to 95% by weight, based on the pharmaceutical composition.

The pharmaceutical composition according to the present invention is preferably a capsule, tablet or coated tablet. More preferably, the pharmaceutical composition according to the present invention is a coated tablet.

The coating may comprise for example hydroxypropylmethylcellulose, polyethylene glycol, talc, and titanium dioxide. Optionally, the coating may comprise a colorant, such as ferric oxide.

The pharmaceutical composition according to the present invention can be prepared by a process comprising a wet granulation step. Examples of wet granulation include wet granulation in a swaying granulator, high shear wet granulation, and fluidized bed granulation. High shear wet granulation is preferred.

A preferable process for preparing the pharmaceutical composition according to the present invention includes the following steps: Copovidone is dissolved in water or an organic solvent (for example ethanol and/or isopropylalcohol) or in a mixture of water and an organic solvent (for example water/ethanol or water/isopropylalcohol mixture). Mannitol is mixed with linagliptin or the pharmaceutically acceptable salt thereof and the copovidone solution is added to the mixture, which is then granulated, optionally sieved, and dried. Magnesium stearate, and optionally crospovidone, is/are added to the dried granulate and the components are mixed. The mixture is finally compressed into tablets.

The pharmaceutical composition according to the present invention can alternatively be prepared by direct compression.

A preferable process for preparing the pharmaceutical composition according to the present invention by direct compression includes the following steps: Linagliptin or the pharmaceutically acceptable salt thereof, mannitol, and copovidone are dry-mixed, for example in a rotary drum mixer. The mixture is optionally milled, for example in a pin mill. Further mannitol is optionally added to the milled mixture. Then, the mixture is compacted, for example by using a roller compactor. The compacted mixture is sieved. Magnesium stearate, and optionally crospovidone, is/are added. After a further mixing step, for example in a rotary drum mixer, the mixture is compressed into tablets, for example by using a Kilian rotary tablet press.

Alternatively, the pharmaceutical composition according to the present invention can be prepared by a process comprising a step of filling a powder comprising linagliptin or a pharmaceutical salt thereof, mannitol, copovidone, magnesium stearate, and optionally crospovidone, into a capsule. The pharmaceutical composition according to the present invention can also be prepared by a process comprising a step of filling granules comprising linagliptin or a pharmaceutical salt thereof, mannitol, copovidone, magnesium stearate, and optionally crospovidone, into a capsule.

The pharmaceutical composition according to the present invention optionally comprises a coating. The coating can be prepared by
  (i) suspending the components of the coating in water, an organic solvent (for example ethanol) or a mixture of water and an organic solvent (for example a water/ethanol mixture),
  (ii) coating the pharmaceutical composition with the thus obtained suspension using a suitable coating device, for example a fluid bed coater or a pan coater, and
  (iii) drying the coated pharmaceutical composition.

In a preferred embodiment, the pharmaceutical composition according to the present invention comprises linagliptin or a pharmaceutically acceptable salt thereof, mannitol, copovidone, and magnesium stearate and is prepared by direct compression.

In a further preferred embodiment, the pharmaceutical composition according to the present invention comprises a core and a coating, wherein the core is prepared by direct compression and comprises linagliptin or a pharmaceutically acceptable salt thereof, mannitol, copovidone, and magnesium stearate.

In a further preferred embodiment, the pharmaceutical composition according to the present invention comprises a core and a coating, wherein the core is prepared by direct compression and comprises linagliptin or a pharmaceutically acceptable salt thereof, mannitol, copovidone, and magnesium stearate, and wherein the coating comprises hydroxypropylmethylcellulose, polyethylene glycol, talc, and titanium dioxide.

In a further preferred embodiment, the pharmaceutical composition according to the present invention comprises linagliptin in amorphous form, mannitol, copovidone, and magnesium stearate and is prepared by direct compression.

In a further preferred embodiment, the pharmaceutical composition according to the present invention comprises a core and a coating, wherein the core is prepared by direct compression and comprises linagliptin in amorphous form, mannitol, copovidone, and magnesium stearate.

In a further preferred embodiment, the pharmaceutical composition according to the present invention comprises a core and a coating, wherein the core is prepared by direct compression and comprises linagliptin in amorphous form, mannitol, copovidone, and magnesium stearate, and wherein the coating comprises hydroxypropylmethylcellulose, polyethylene glycol, talc, and titanium dioxide.

In a further preferred embodiment, the pharmaceutical composition according to the present invention comprises a mixture of crystalline linagliptin having polymorphic form A and crystalline linagliptin having polymorphic form B, mannitol, copovidone, and magnesium stearate and is prepared by direct compression.

In a further preferred embodiment, the pharmaceutical composition according to the present invention comprises a core and a coating, wherein the core is prepared by direct compression and comprises a mixture of crystalline linagliptin having polymorphic form A and crystalline linagliptin having polymorphic form B, mannitol, copovidone, and magnesium stearate.

In a further preferred embodiment, the pharmaceutical composition according to the present invention comprises a core and a coating, wherein the core is prepared by direct compression and comprises a mixture of crystalline linagliptin having polymorphic form A and crystalline linagliptin having polymorphic form B, mannitol, copovidone, and magnesium stearate, and wherein the coating comprises hydroxypropylmethylcellulose, polyethylene glycol, talc, and titanium dioxide.

In a further preferred embodiment, the pharmaceutical composition according to the present invention comprises crystalline linagliptin having polymorphic form A, mannitol, copovidone, and magnesium stearate and is prepared by direct compression.

In a further preferred embodiment, the pharmaceutical composition according to the present invention comprises a core and a coating, wherein the core is prepared by direct compression and comprises crystalline linagliptin having polymorphic form A, mannitol, copovidone, and magnesium stearate.

In a further preferred embodiment, the pharmaceutical composition according to the present invention comprises a core and a coating, wherein the core is prepared by direct compression and comprises crystalline linagliptin having polymorphic form A, mannitol, copovidone, and magnesium stearate, and wherein the coating comprises hydroxypropylmethylcellulose, polyethylene glycol, talc, and titanium dioxide.

Another embodiment of the present invention relates to a container comprising the pharmaceutical composition according to the present invention, wherein the container is prepared from a material having a permeability for water vapor as measured according to DIN 53122 of from 1.0 $g*m^{-2}*d^{-1}$ to 5000 $g*m^{-2}*d^{-1}$. A preferred container is a blister package, wherein the blister is made from polyvinyl chloride, polystyrene, polyamide, polyethylenevinylacetate, cellophane and/or celluloseacetate.

The pharmaceutical composition of the present invention can be used for the treatment of metabolic disorders including pre-diabetes, glucose intolerance, pathological fasting glucose, hyperglycemia, type II diabetes mellitus, type I diabetes mellitus, gestational diabetes, disorders associated with type II diabetes mellitus, type I diabetes mellitus or gestational diabetes, such as wound healing disorders, obesity, diabetic foot, diabetes-associated ulcer, diabetic hyperlipidemia, diabetic dyslipidemia. The pharmaceutical composition of the present invention can further be used for supporting allograft transplantation, in particular transplantation of islets of Langerhans or beta cells. The pharmaceutical composition of the present invention can also be used for the treatment of osteoporosis, rheumatoid arthritis, osteoarthritis, neurotraumatic diseases, pain, migraine, acne, proliferative skin diseases, such as psoriasis, hyperproliferative diseases, cardiac hypertrophy, cirrhoses, and fibromatoses.

The pharmaceutical composition of the present invention can comprise a further active ingredient selected from active ingredients that lower the blood sugar level, active ingredients that lower the lipid level in the blood, active ingredients that raise the HDL (high density lipoprotein) level in the blood, active ingredients that lower blood pressure, active ingredients that are indicated in the treatment of obesity, and active ingredients that are indicated in the treatment of atherosclerosis.

Examples of further active ingredients that lower the blood sugar level include biguanides, thiazolidindiones, sulfonylureas, glinides, inhibitors of alpha-glucosidase, GLP-1 or GLP-1 analogues, insulin, and insulin analogues.

A preferred further active ingredient is metformin hydrochloride.

In a particularly preferred embodiment, the pharmaceutical composition of the present invention comprises linagliptin or a pharmaceutically acceptable salt thereof, metformin or a pharmaceutically acceptable salt thereof, mannitol, copovidone, and magnesium stearate.

In another preferred embodiment, the pharmaceutical composition of the present invention comprises linagliptin or a pharmaceutically acceptable salt thereof, metformin or a pharmaceutically acceptable salt thereof, mannitol, copovidone, crospovidone, and magnesium stearate.

EXAMPLES

The X-ray powder diffractogram (XRPD) was obtained with a PANalytical X'Pert PRO diffractometer equipped with a theta/theta coupled goniometer in transmission geometry, Cu-K$\alpha$1,2 radiation (wavelength 0.15419 nm) with a focusing mirror and a solid state PIXcel detector. The pattern was recorded at a tube voltage of 45 kV and a tube current of 40 mA, applying a step size of 0.013° 2-theta with 80 s per step (255 channels) in the angular range of 2° to 40° 2-theta at ambient conditions.

The Fourier transform infrared (FTIR) spectrum was recorded on an MKII Golden Gate# Single Reflection Diamond ATR (attenuated total reflection) cell with a Bruker Tensor 27 FTIR spectrometer with 4 cm$^{-1}$ resolution at ambient conditions. To record a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$.

Ambient temperature is a temperature in the range of from 20 to 25° C.

Example 1

5.4 g Copovidone (Kollidon VA64, Luviskol), 5.0 g linagliptin in amorphous form and 50.0 g mannitol are dry mixed in a rotary drum mixer for about 10 min to produce a pre-mix. The pre-mix is milled for about 10 min with a pin mill. 116.9 g Mannitol is added to the pre-mix, and mixed for about 10 min in a rotary drum mixer. This mixture is compacted on a roller compactor (Alexander Compactor). The compacted mixture is passed through a 1.0 mm sieve. 0.69 g Magnesium stearate is added and the components are mixed for about 1 min in a rotary drum mixer. The mixture is finally compressed into tablet cores using a Kilian rotary tablet press.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a pan-coater to a weight gain of 5 mg/tablet to produce film-coated tablets.

Each tablet contains 5 mg linagliptin.

Example 2

1.38 g Copovidone (Kollidon VA64, Luviskol) is dissolved in 7.81 g water. 1.28 g Linagliptin in amorphous form is sieved though a 1 mm sieve into a mixer (Diosna mixer). 42.93 g Mannitol is sieved through a 1 mm sieve into the mixer containing the linagliptin. The compounds are dry mixed for about 10 min. The copovidone solution is added to the mixture during about 15 min. The mixture is granulated using a high shear mixer for 3 to 10 min and is then passed through a 2 mm sieve. The sieved granulate is dried in an oven at 55° C. until constant weight (loss on drying: 0.5 to 4% by weight). The dried granulate is passed through a 1 mm sieve. 0.92 g Crospovidone (Poliplasdone XL) and 0.69 g magnesium stearate are added and the components are mixed for about 1 min in a rotary drum mixer. The mixture is finally compressed into tablet cores.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a pan-coater to a weight gain of 5 mg/tablet to produce film-coated tablets.

Each tablet contains 5 mg linagliptin.

Example 3

5.4 g Copovidone (Kollidon VA64, Luviskol) is dissolved in 40 g water. 5.0 g Linagliptin in amorphous form is sieved through a 1 mm sieve into a mixer (Diosna mixer). 166.9 g Mannitol is sieved though a 1 mm sieve into the mixer containing the linagliptin. The compounds are dry mixed for about 10 min to produce a pre-mix. The copovidone solution is added to the mixture during 15 min. The mixture is granulated using a high shear mixer for 3 to 10 min and is then passed through a 2 mm sieve. The sieved granulate is dried in an oven at 55° C. until constant weight (loss on drying: 0.5 to 4% by weight). The dried granulate is passed through a 1.0 mm sieve. 0.69 g Magnesium stearate is added and the components are mixed for about 1 min in a rotary drum mixer. The mixture is finally compressed into tablet cores.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a pan-coater to a weight gain of 5 mg/tablet to produce film-coated tablets.

Each tablet contains 5 mg linagliptin.

Example 4

5.4 g Copovidone (Kollidon VA64, Luviskol) is dissolved in 40 g water. 5.0 g Crystalline linagliptin having polymorphic form A is sieved though a 1 mm sieve into a mixer (Diosna mixer). 166.9 g Mannitol is sieved through a 1 mm sieve into the mixer containing the linagliptin. The compounds are dry mixed for about 10 min to produce a pre-mix. The copovidone solution is added to the mixture during 15 min. The mixture is granulated using a high shear mixer for 3 to 10 min and is then passed through a 2 mm sieve. The sieved granulate is dried in an oven at 55° C. until constant weight (loss on drying: 0.5 to 4% by weight). The dried granulate is passed through a 1.0 mm sieve. 0.69 g Magnesium stearate is added and the components are mixed for about 1 min in a rotary drum mixer. The mixture is finally compressed into tablet cores.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a pan-coater to a weight gain of 3% by weight to produce film-coated tablets.

Each tablet contains 5 mg linagliptin.

Example 5

5.4 g Copovidone (Kollidon VA64, Luviskol), 2.5 g crystalline linagliptin having polymorphic form A, 2.5 g crystalline linagliptin having polymorphic form B and 50.0 g mannitol are dry mixed in a rotary drum mixer for about 10 min to produce a pre-mix. The pre-mix is milled for about 10 min with a pin mill. 116.9 g Mannitol is added to the pre-mix, and mixed for about 10 min in a rotary drum mixer. This mixture is compacted on a roller compactor (Alexander Compactor). The compacted mixture is passed through a 1.0 mm sieve. 0.69 g Magnesium stearate is added and the components are mixed for about 1 min in a rotary drum mixer. The mixture is finally compressed into tablet cores using a Kilian rotary tablet press.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a pan-coater to a weight gain of 5 mg/tablet to produce film-coated tablets.

Each tablet contains 5 mg linagliptin.

Example 6

5.4 g Copovidone (Kollidon VA64, Luviskol), 5.0 g linagliptin in amorphous form and 50.0 g mannitol are dry mixed in a rotary drum mixer for about 10 min to produce a pre-mix. The pre-mix is milled for about 10 min with a pin mill. 116.9 g Mannitol is added to the pre-mix, and mixed for about 10 min in a rotary drum mixer. This mixture is compacted on a roller compactor (Alexander Compactor). The compacted mixture is passed through a 1.0 mm sieve. 0.69 g Magnesium stearate and 3.6 g crospovidone are added and the components are mixed for about 1 min in a rotary drum mixer. The mixture is finally compressed into tablet cores using a Kilian rotary tablet press.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a pan-coater to a weight gain of 5 mg/tablet to produce film-coated tablets.

Each tablet contains 5 mg linagliptin.

Example 7

5.4 g Copovidone (Kollidon VA64, Luviskol), 5.0 g crystalline linagliptin having polymorphic form C, and 50.0 g mannitol are dry mixed in a rotary drum mixer for about 10 min to produce a pre-mix. The pre-mix is milled for about 10 min with a pin mill. 116.9 g Mannitol is added to the pre-mix, and mixed for about 10 min in a rotary drum mixer. This mixture is compacted on a roller compactor (Alexander Compactor). The compacted mixture is passed through a 1.0 mm sieve. 0.69 g Magnesium stearate is added and the components are mixed for about 1 min in a rotary drum mixer. The mixture is finally compressed into tablet cores using a Kilian rotary tablet press.

2.5 g Hydroxypropyl methylcellulose, 0.25 g polyethylene glycol, 0.875 g talc, 1.25 g titanium dioxide and 0.125 g iron oxide are suspended in 25 g water at ambient temperature to produce a coating suspension. The tablet cores are coated with the coating suspension in a fluid-bed coater to a weight gain of 5 mg/tablet to produce film-coated tablets.

Each tablet contains 5 mg linagliptin.

Example 8

98.8 mg linagliptin polymorph A is dissolved in 5 ml dichloromethane at ambient temperature. The clear solution is evaporated to dryness at 40° C. and ≤800 mbar. The obtained solid is dried at ambient temperature under vacuum (≤40 mbar) for about 21 hours to obtain amorphous linagliptin quantitatively.

Figure 2:
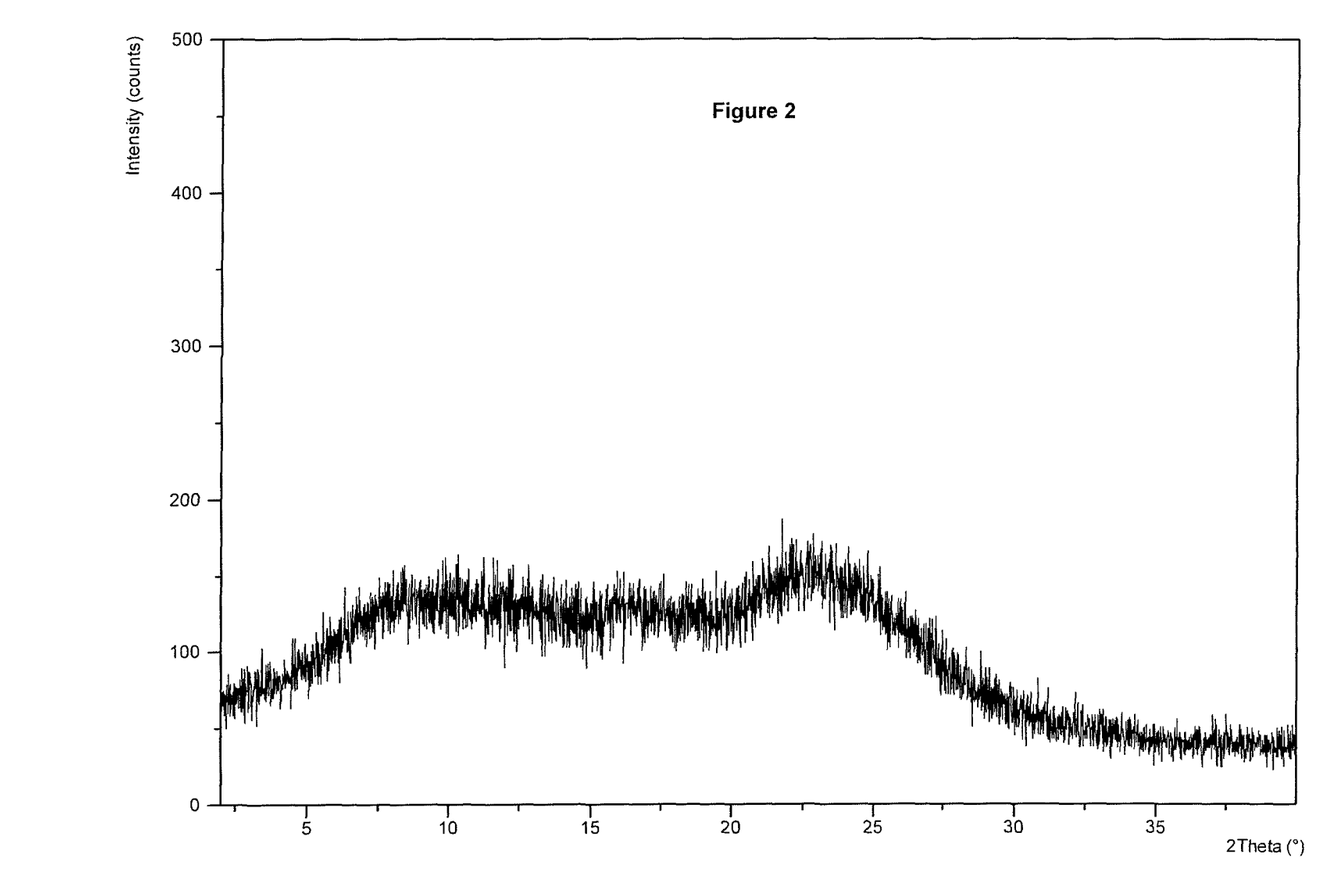
FIG. 2: X-Ray powder diffractogram (XRPD) of amorphous linagliptin prepared according to Example 8

The XRPD of the obtained material shows an amorphous halo as can be seen from FIG. 2.

The amorphous linagliptin prepared according to example 8 shows the following FTIR peaks:

| wavenumber [cm$^{-1}$] |
| --- |
| 2923 |
| 2851 |
| 1698 |
| 1650 |
| 1615 |
| 1568 |
| 1508 |
| 1434 |
| 1398 |
| 1344 |
| 1282 |
| 1128 |
| 947 |
| 759 |
| 613 |

Reference Example 1

5.4 g Copovidone is dissolved in purified water at ambient temperature to produce a granulation liquid. 5.0 g Linagliptin, 130.9 g mannitol, 18.0 g pregelatinized starch and 18.0 g corn starch are blended in a mixer to produce a pre-mix. The pre-mix is moistened with the granulation liquid and subsequently granulated using a high shear mixer. The granulate is dried at about 60° C. in a fluid bed dryer until a loss on drying value of 2 to 4% by weight is obtained. The dried granulate is sieved through a sieve with a mesh size of 1.0 mm. 2.7 g Magnesium stearate is passed through a 1.0 mm sieve and added to the granulate. Subsequently the final blend is compressed into tablet cores.

2.5 g Hydroxypropyl methylcellulose, 0.25 g polyethylene glycol, 0.875 g talc, 1.25 g titanium dioxide and 0.125 g iron oxide are suspended in purified water in a mixer at ambient temperature to produce a coating suspension. The tablet cores are coated with the coating suspension to a weight gain of 3% by weight to produce film-coated tablets.

The storage stability of the compositions was tested.

The tablets were stored under the following conditions: 1. Protected conditions: The tablets were stored in moisture-tight unit dose blisters made of aluminum/polyvinyl chloride/polyvinyl acetate copolymer-acrylate at ambient temperature. 2. Ambient conditions: The tablets were stored in a closed glass container at 50% relative humidity for 3 days at ambient temperature. 3. High humidity conditions: The tablets were stored in a closed glass container at 95% relative humidity for 3 days at ambient temperature.

The dissolution of the tablets was determined in a paddle apparatus containing 6 identical vessels and stirring apparatuses to allow simultaneous analysis of six tablets (SOTAX AT 7). The measurements were made at 37±0.5° C. with a paddle speed of 50±3 rpm in 900 ml 0.1 n HCl as dissolution medium (pH 1.2). Every 3 minutes, a sample was taken from each of the vessels. The sample was taken from the zone midway between the surface of the dissolution medium and the top of the rotating paddles, not less than than 1 cm from the vessel wall. The sample was injected into a UV analyzer (Agilent 8453, Agilent Technologies) to determine the amount of the dissolved active ingredient linagliptin. The amount of the detected linagliptin in percent [%] based on the original amount of the linagliptin present in the tablet used for the dissolution test measured every 3 minutes is given in the below table. The volume change after taking a sample was considered:

| | Percentage of dissolution [%] | | | | |
|---|---|---|---|---|---|
| | Example 1 | | | Reference Example 1 | |
| Time [min] | Protected conditions | Ambient conditions | High humidity conditions | Protected conditions | High humidity conditions |
| 0 | 0 | 0 | 0 | 0 | 0 |
| 3 | 7.0 | 12.6 | 39.8 | 4.4 | 7.2 |
| 6 | 20.7 | 33.7 | 96.3 | 33.6 | 14.6 |
| 9 | 31.5 | 52.4 | 98.5 | 61.1 | 20.5 |
| 12 | 40.8 | 67.6 | 98.3 | 81.9 | 25.0 |
| 15 | 50.6 | 79.4 | 98.4 | 95.0 | 28.8 |
| 18 | 59.0 | 88.0 | 98.5 | 98.9 | 32.5 |
| 21 | 66.7 | 93.4 | 98.1 | 98.9 | 35.7 |
| 24 | 74.4 | 95.5 | 98.4 | 98.9 | 38.3 |
| 27 | 79.5 | 95.7 | 98.3 | 99.1 | 41.0 |
| 30 | 84.6 | 95.6 | 98.3 | 99.2 | 43.7 |

Figure 1:
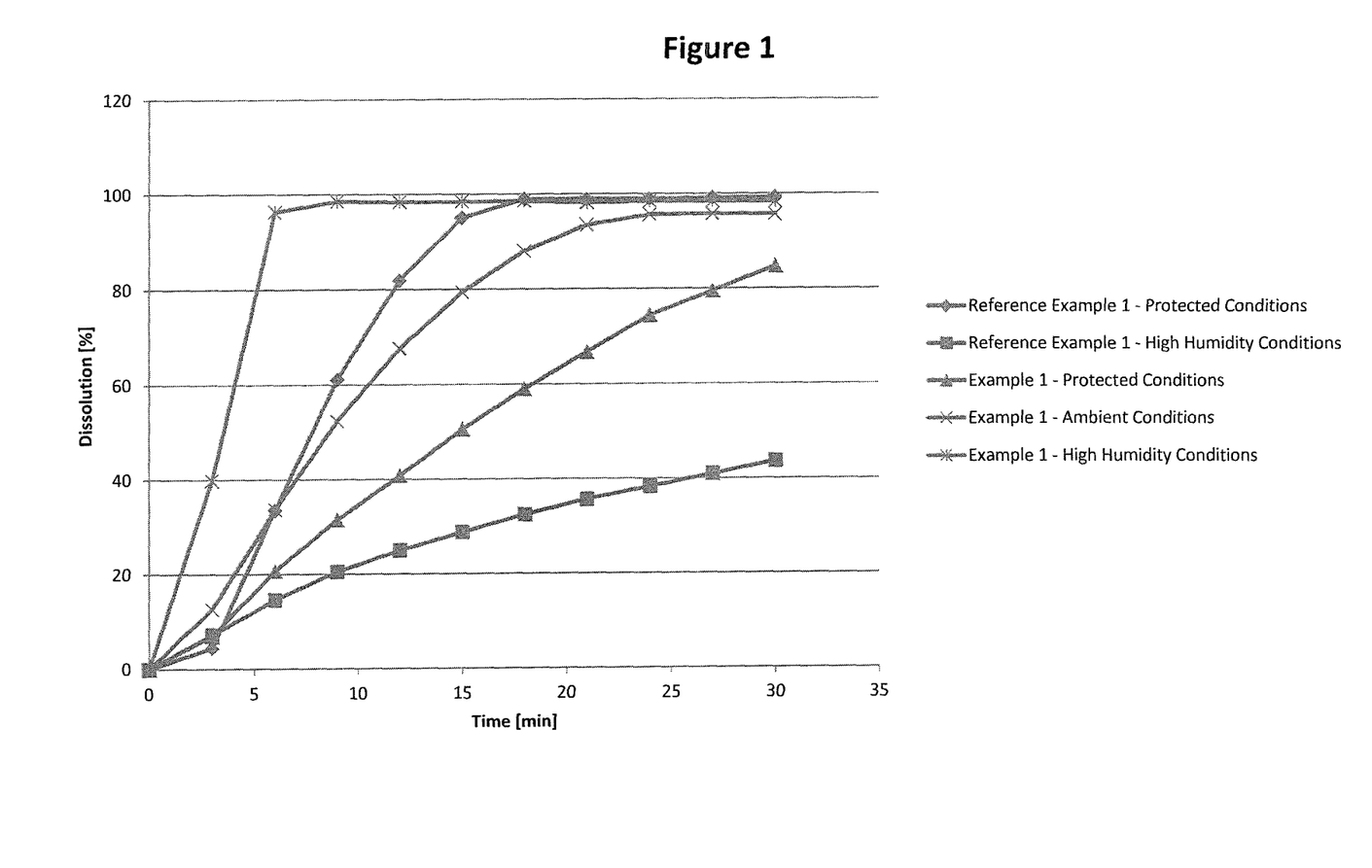
FIG. 1: Dissolution profiles of the pharmaceutical composition according to WO2007/128724 (Reference Example 1) stored under protected conditions and under high humidity conditions, and dissolution profiles of the pharmaceutical composition according to the present invention (Example 1) under protected conditions, ambient conditions and under high humidity conditions

The dissolution curves are shown in FIG. 1. It can be seen that the pharmaceutical composition according to WO2007/128724 (Reference Example 1) shows a rapid dissolution if stored under moisture-tight conditions. However, after storage for 3 days at 95% relative humidity, the formulation dissolves rather slowly and after 30 minutes less than 50% of the formulation dissolved. That means, less than half of the active ingredient is available for absorption after 30 minutes. Therefore, the bioavailability of the active ingredient is far below the acceptable level.

It can further be seen from FIG. 1 that the pharmaceutical composition of the present invention according to Example 1 surprisingly shows a completely different dissolution behavior compared to the pharmaceutical composition according to WO2007/128724 (Reference Example 1).

Under protected conditions, the dissolution is slow and reaches about 85% after 30 min. After storage at ambient conditions, the pharmaceutical composition according to Example 1 shows a dissolution behavior comparable to the pharmaceutical composition according to WO2007/128724 (Reference Example 1) when stored in the absence of moisture. That means, the pharmaceutical composition of the present invention can be stored under ambient conditions without any expensive moisture-tight packaging while the pharmaceutical composition according to WO2007/128724 has to be protected from moisture. Furthermore, after storage at 95% relative humidity for 3 days, the dissolution of the pharmaceutical composition according to Example 1 is not reduced, to the contrary, it is unexpectedly improved. In other words, the pharmaceutical composition of the present invention shows an even better bioavailability when stored under high humidity conditions compared to the same pharmaceutical composition when stored under dry conditions. More importantly, the pharmaceutical composition of the present invention does not show the reduced dissolution which is characteristic for the pharmaceutical composition according to WO2007/128724 (Reference Example 1). Thus, the pharmaceutical composition of the present invention is characterized by a high bioavailability and is effective in the treatment of the above-mentioned disorders even if it has been produced, handled and/or stored under high humidity conditions.

The invention claimed is:

1. A coated pharmaceutical composition comprising:
    a composition comprising linagliptin or a pharmaceutically acceptable salt thereof as active ingredient;
    mannitol;
    copovidone; and
    magnesium stearate, wherein the mannitol is present in an amount greater than 90 to 95% by weight, based on the weight of the pharmaceutical composition; and
    a coating comprising hydroxypropylmethylcellulose on the composition.

2. The coated pharmaceutical composition according to claim 1, further comprising crospovidone.

3. The coated pharmaceutical composition according to claim 1, further comprising a second active ingredient.

4. The coated pharmaceutical composition according to claim 3, wherein the second active ingredient is metformin hydrochloride.

5. The coated pharmaceutical composition according to claim 1, further comprising a core consisting of linagliptin or a pharmaceutically acceptable salt thereof, mannitol, copovidone and magnesium stearate.

6. The coated pharmaceutical composition according to claim 2, further comprising a core consisting of linagliptin or a pharmaceutically acceptable salt thereof, mannitol, copovidone, crospovidone and magnesium stearate.

7. The coated pharmaceutical composition according to claim 1, wherein the coating comprises hydroxypropylmethylcellulose, polyethylenglycol, talc, titanium dioxide, and optionally a colorant.

8. The coated pharmaceutical composition according to claim 1 wherein the linagliptin is present as amorphous linagliptin, crystalline linagliptin having polymorphic form A, crystalline linagliptin having polymorphic form B and/or crystalline linagliptin having polymorphic form C.

9. The coated pharmaceutical composition according to claim 8, wherein the linagliptin is present as a mixture of crystalline linagliptin having polymorphic form A and crystalline linagliptin having polymorphic form B.

10. An amorphous linagliptin according to claim 8.

11. An amorphous linagliptin according to claim 10 having an FTIR spectrum comprising characteristic peaks at $2923\pm2^{cm-1}$ $1650\pm2^{cm-1}$, $1568\pm2^{cm-1}$ $1344\pm2^{cm-1}$ and $759\pm2^{cm-1}$.

12. A process for preparing the coated pharmaceutical composition according to claim 1 comprising directly compressing the composition of claim 1 and applying the coating to the compressed composition.

13. A container comprising the coated pharmaceutical composition according to claim 1, wherein the container is prepared from a material having a permeability for water vapor as measured according to DIN 53122 of from 1.0 $g*m^{-2}*d^{-1}$ to 5000 $g*m^{-2}*d^{-1}$.

14. The container according to claim 13, which is a blister package, wherein the blister is made from polyvinylchloride, polystyrene, polyamide, polyethylenevinylacetate, cellophane and/or celluloseacetate.

15. A coated compressed tablet of a pharmaceutical composition comprising:
 a composition comprising linagliptin or a pharmaceutically acceptable salt thereof as active ingredient;
 mannitol;
 copovidone; and
 magnesium stearate, wherein the mannitol is present in an amount greater than 90 to 95% by weight, based on the weight of the pharmaceutical composition, wherein the composition is in the form of a directly compressed tablet; and
 a coating comprising hydroxypropylmethylcellulose on the directly compressed tablet.

16. The coated compressed tablet according to claim 15, wherein the coating comprises hydroxypropylmethylcellulose, polyethylenglycol, talc, titanium dioxide, and optionally a colorant.

17. The coated compressed table according to claim 15, wherein the coated tablet is stored in a package that is not moisture-tight.

18. The coated compressed tablet according to claim 17, wherein the container is prepared from a material having a permeability for water vapor as measured according to DIN 53122 of from 1.0 $g*m^{-2}*d^{-1}$ to 5000 $g*m^{-2}*d^{-1}$.

19. The coated compressed tablet according to claim 15, wherein the coated tablet is stored in a blister package.

20. The coated compressed tablet according to claim 19, wherein the blister package is formed from polyvinylchloride, polystyrene, polyamide, polyethylenevinylacetate, cellophane and/or celluloseacetate.

21. The coated compressed tablet according to claim 19, wherein the coated compressed tablet has resistance to degradation of the active ingredient caused by moisture.

* * * * *